United States Patent [19]

Flores de Castañeda

[11] Patent Number: 5,459,042
[45] Date of Patent: Oct. 17, 1995

[54] **PROCEDURE TO PRESERVE ANTIGENS OF *ENTAMOEBA HISTOLYTICA* WITHOUT ENZYMATIC INHIBITORS**

[76] Inventor: Maria D. S. Flores de Castañeda, Palomas 501, San Jemo, Monterrey, N.L. 64630, Mexico

[21] Appl. No.: 139,290

[22] Filed: Oct. 20, 1993

[30] Foreign Application Priority Data

Oct. 20, 1992 [MX] Mexico ................................. 926019

[51] Int. Cl.$^6$ ................................................ G01N 33/569
[52] U.S. Cl. ........................... 435/7.22; 435/29; 435/961; 435/967; 436/518; 436/174; 436/175; 436/176; 530/422; 530/822
[58] Field of Search .................................. 435/7.22, 961, 435/962, 967, 29; 436/518, 530, 174, 175, 176; 530/422, 822

OTHER PUBLICATIONS

Arguello–Garcia et al., "Evaluation of an immunoblot methodology for the detection of relevant *Entamoeba histolytica* antigens by antibodies induced in human amebiasis," Arch, Invest. Med., 21:3–9 (1990).

S. Said–Fernadez, et al., Zeitschrift Fur Parasitenkunde 56, 219–225 (1978).

H. M. Mathews, et al., *J. Protozool.*, 33 (3), (1986), pp. 328–334.

Shiv Pillai, et al., *Gastroenterology*, 83, (1982), pp. 1210–1214.

Agneta Aust Kettis, et al., *Am. J. Trop. Med. Hyg.*, 32 (3), (1983), pp. 512–521.

Eva E. Avila, et al., *J. Protozool.*, 32 (1), (1985), pp. 163–166.

*Primary Examiner*—Carol E. Bidwell
*Attorney, Agent, or Firm*—Gunn, Lee & Miller

[57] ABSTRACT

The invention relates methods of determining *Entamoeba histolytica* antigenic reference patterns of proteins recognized by sera from patients having amebic liver abscesses, patients having intestinal amebiasis and patients negative for any amebic disease and methods using these antigenic reference patterns for aiding in the differential diagnosis of a patient with amebic liver abscesses or intestinal ambiasis by detecting the presence of antibodies in a sample of human serum which bind to *Entamoeba histolytica* proteins identified in the antigenic reference patterns.

16 Claims, 4 Drawing Sheets

PROCEDURE TO PRESERVE ANTIGENS OF *ENTAMOEBA HISTOLYTICA* WITHOUT ENZYMATIC INHIBITORS

BACKGROUND OF THE INVENTION

Amebiasis is a parasitism provoked by the protozoan *Entamoeba histolytica*. It affects mainly the inhabitants of developing countries. Under appropriate conditions which are not well known, trophozoites differentiate to an infective form or cyst which is excreted with excrements and this waycan infect a new host by oral food, water or person to person transmission. Most of the people infected with *Entamoeba histolytica* are asymptomatic, but in 10% of the people with amebiasis, the parasite produces sickness when it invades the intestinal mucosity producing amoebic colitis or more dangerous damage when the amebiasis is extraintestinal and there is a dissemination of the protozoan to the liver, provoking an amoebic liver abscess. In the cases in which there is a perforation of the liver or the intestine, it can provoke pleural damage, pericarditis, peritonitis and even death. Amebiasis occupies the sixth place among the most frequent causes of death in Mexico. In Mexico as in Venezuela 2% to 15% of the cases of children with diarrhea which have been subjected to hospitalization, have been associated with an *Entamoeba histolytica* infection.

To effect correct epidemiological studies, it will require the development of diagnostic methods which are sensitive and specific. The coproparasitoscopic diagnosis of *Entamoeba histolytica* is especially difficult because it requires highly skilled workers to prevent false interpretations. The serologic diagnosis is not effective because the existing tests are not sensitive enough, especially when they are used in highly endemic zones. To obtain really useful diagnostic tests, it is necessary to know the amoebic molecules that are actively involved in the cases of invasive amebiasis and to generate with these molecules effective diagnostic tests. Knowing these molecules, studies can be made on their intervention in the immune protection mechanisms generated against amoebas and the possible implementation of vaccines. A major impediment to achieve this goal is represented by the highly elevated enzymatic activity of the proteases present in the amoebic extracts (McLaughlin & Faubert, G., 1977, "Partial purification and some properties of a neutral sulfhydril and an acid proteinase from *Entamoeba histolytica*" are disclosed in Canadian Journal of Microbiology, 23, 420-425, and Perez-Monfort, Ostoa-Saloma, P. Velazquez-Medina, L. Montort I & Becker, I., 1987, "Catalytic classes of proteinases of *Entamoeba histolytica*" Molecular and Biochemical Parasitology, 6, 87–97). The proteases degrade proteins in the amoebas giving random products of degradation and make, if not impossible at least very difficult, to standarize the methods of fine analysis of antigenicity. To avoid the enzyme activity, enzymatic inhibitors are used, but they have the inconvenience that they are not totally effective, that they permit working with extracts only for relatively short periods of time and they do not give the opportunity to store the same samples for later tests. The procedures that we wish to patent is based on the method to remove the lipids, described by Said-Fernandez, S. and Lopez-Revilla R. (Said-Fernandez, S and Lopez-Revilla R. (1979) "Characteristic protein electrophoretic patterns of four Entamoeba strains", (Zeitschrift für Parasitenkunde, 56. 219–225). The method of the invention relates to the preservation of amoebic antigens, without using enzymatic inhibitors, which is the method presently used to preserve amebic antigens for further study.

SUMMARY OF THE INVENTION

The method of the invention relates to the preservation of the antigens of a certain microorganism without using enzymatic inhibitors, although, by no means restrictive to *E. histolytica*. The enzymatic activity of the proteases which are contained by *E. histolytica* makes the study of the amoebic molecules that are antigenically important difficult. This is why one of the objectives of the present invention is to use *Entamoeba histolytica* as a model of the parasite. Another objective of the present invention is to reduce the action of the enzymes of the protozoan without enzymatic inhibitors, A further objective is to compare the results obtained with the method of the invention with those obtained with conventional methods in which enzymatic inhibitors are used and show this is the best. The method is based on obtaining an insoluble amoebal extract in polar solvents or their mixtures and subject it to heating in a boiling water bath, for times of 5 to 20 minutes, obtaining a greater reduction in enzymatic activity than that attained with enzymatic inhibitors. The procedure of the present invention preserves the antigenicity of the amoebal molecules, since they are recognized by the antibodies present in the sera of individuals with amoebic hepatic abscess. The procedure can be not only of great help in the analysis and identification of antigenic molecules of amoebas and to the study the immunologic response against *Entamoeba histolytica*, but also it has many uses: for example, but not restricted to obtain molecules to prepare a vaccine, or to prepare diagnostic kits for amebiasis, invasive or noninvasive, followed by the opportune treatment of this disease.

DETAILED DESCRIPTION OF THE INVENTION

Figure 1:
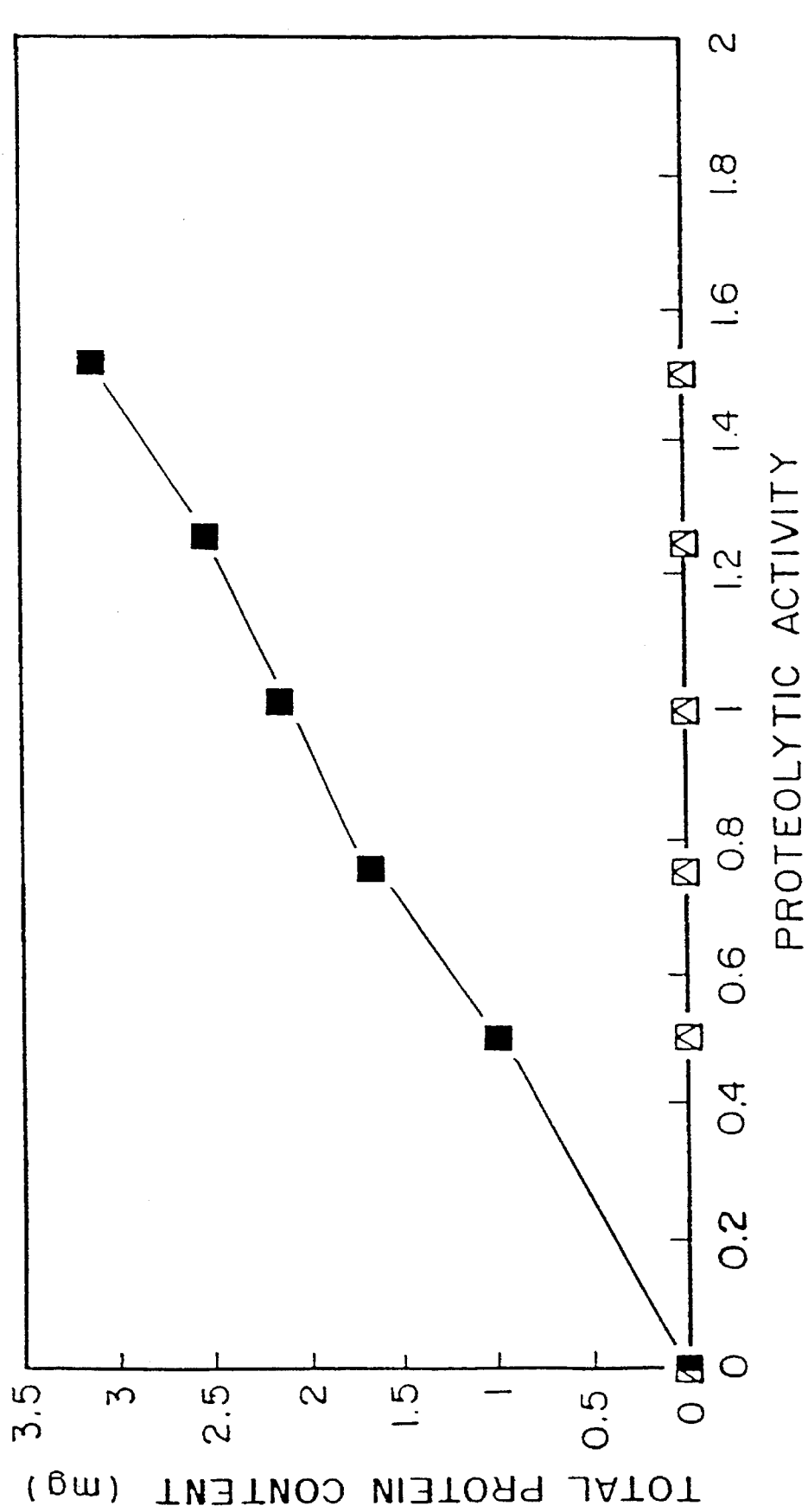
FIG. 1 represents a graph in which the relationship between the protein content of the crude extracts and its proteolytic activity on azocasein is analyzed and is compared with the IC:MC fraction in the presence and absence of 2% SDS and 5% 2-ME. The figure depicts the activity of crude extract ■—■, IC:MC □—□, and IC:MC+2% SDS and 5% 2-ME (2-mercaptoethanol) ∆—∆. The activity of 0.5 mg crude extract protein is normalized to the unit (Unit= 0.320 O.D.).

In the invention procedure trophozoites of the strain *Entamoeba histolytica* HK-9 were used which were cultured and provided by Dr. Salvador Said-Fernandez of Centro de Investigaciones Biomédicas del Noreste del Instituto Mexicano del Seguro Social (IMSS). The trophozoites were cultured axenically as has been described by SAID-FERNANDEZ et al. (Said-Fernandez, S., Vargas-Villarreal, J. Castro-Garza, J., MataCardenas, B., Navarro-Marmolejo, L. Lozano-Garza, F. & MartinezRodriguez, H (1988). PEHPS medium: an alternative for axenic cultivation of *Entamoeba histolytica* and *E. invadens*. Transactions of the Royal Society for Tropical Medicine and Hygiene 82, 249–253). The trophozoites were used immediately or were lyophilized and stored until use. The protein contents was determined according to the method of Lowry et al. (Lowry H., Rosegroug, N. J., Farr, A. L. & Randall, R. J. (1951). "Protein measurement with the Folin phenol reagent", Journal of Biological Chemistry, 193, 265–275).

OBTAINING THE EXTRACT WHICH CONTAINS THE INSOLUBLE FRACTION IN POLAR SOLVENTS OR THEIR MIXTURES (chloroform, methanol, ether, ethanol). The polar solvent insoluble fraction can be obtained by treating trophozoites with a polar solvent, such as chloroform, methanol, ethanol, ether or mixtures thereof. Preferably, the trophozoites are resuspended in ranges comprising between 5 to 100 vol. of chloroform:methanol in a volume proportion comprising between 1:1 to 20:1 and inclusively 1:20. The mixture is stirred, centrifuged at least two minutes at 400×g at 4° C. The supernatant is discarded and the operation can be repeated several times. When the fraction IC:M is obtained, it is vacuum dried and frozen minimally at −20° C. until its use. Afterwards the IC:M fraction is resuspended in a buffer with pH ranging from 4 to 9, and it is heated in a boiling water bath, for several minutes for maximum of 20 minutes. The treated IC:M fraction forms the IC:MC fraction, which is ready to use and may be preserved at −20° C. for periods up to several months.

As established in the objectives; the reduction in proteolytic activity in the IC:MC fraction in the absence of enzymatic inhibitors was demonstrated and the method of the invention was compared with the conventional method using an enzymatic inhibitor (iodoacetamide) to reduce the proteolytic activity of crude amebic extracts. The crude extract was useful as a positive enzymatic activity control. To obtain crude extracts, the trophozoites were resuspended and diluted to a concentration of 5 mg/ml protein or more, the mixture was stirred and submitted to ultrasonic vibration; was centrifuged at 400×g for 5 minutes, the sediment was discarded and the supernatant was used in the experiments realized.

There were 2 methods used to determine the proteolytic activity in the crude extracts and in the IC:MC fraction. In the former as substrate azocasein was used and in the latter hide powder azure. In the first method the experiments were based on the reports of Mc LAUGHLIN J. & FAUBERT, G. and AVILA E. et al. (Mc LAUGHLIN, J. & FAUBERT, G. (1977)), "Partial purification and some properties of a neutral sulfhydril and an acid proteinase from *Entamoeba histolytica*", Canadian Journal of Microbiology, 23, 420–425; AVILA E., E., Sanchez-Garza, M & Calderon J. (1985), "*Entamoeba histolytica* and *E. invadens*: Sulfhydril-dependent proteolytic activity", Journal of Protozoology, 32, (163–166). The crude extract was resuspended to a protein concentration of 25 mg/ml in 0.05M Tris-HCl, pH 7.6 at a range comprising of 1:1 to 20:1 and also 1:20 with 0.5% Triton X-100 and was incubated 1 hour at 4° C. The samples were centrifuged at 400×g for 2 minutes and the supernatants were recuperated for analysis. The IC:MC fraction was treated the same way as the crude extract. To some of the samples 2% of SDS and 10% of 2-ME were added. These substances are used in electrophoretic techniques on polyacrilamide gels in the presence of sodium dodecylsulphate (SDS-PAGE). Avila et. al. have reported that SDS and 2-ME stimulate the proteolytic activity of the amebic enzymes. With each sample of the different extracts serial dilutions were made from 0.5 to 1.5 mg of total proteins at 150 μl 0.05M Tris-HCL pH 7.5 and 100 μl azocasein 1% were added, and incubated for 90 minutes at 37° C. 250 μl trichloroacetic acid 10% were added to each probe and centrifuged at 7000×g for 6 minutes. To each 200 μl of supernatant 1.8 ml NaOH 0.5N were added and the absorbency of each sample was read at 420 nm on a PMQ II Zeiss PMQ III spectrophotometer (Zeiss, Germany). As positive control trypsin was used (300 ug for each reaction mixture).

FIG. 1 shows that the proteolytic activity of the crude extract on casein corresponds to a linear relationship wit respect to the dose. In contrast, with doses equivalent to that of the crude extracts with the IC:MC fraction there was no observed enzymatic activity, not even in the presence of SDS and 2-ME.

The second method was carried out according to Rinderknecht et al. (Rinderknecht H., Geokas, M. C., Silverman, P. & Haverback, B. J. 1968. "A new ultrasensitivity method for the determination of proteolytic activity", Clinica Chimica Acta, 21, 197–203). The activity corresponding to 6 million trophozoites was tested. Crude amebic extracts, IC:M and IC:MC were used. The samples were resuspended in 1.5 ml 0.05M Tris-HCL pH 7.5 containing 0.5% triton X-100, they were incubated for one hour at 4° C. and centrifuged at 11000×g for 15 minutes. 1 ml of the supernatant was added to 1 ml Tris-HCl containing 5 mg hide powder azure and 100 μl cysteine 0.2M. The samples were incubated at 37° C./for 1 hour; at the end of which the reaction was stopped by putting the tubes in an ice water bath. They were cold-centrifuged for 5 minutes at 450×g. The absorbency of the supernatants was determined at a wavelength of 600 nm. The former treatment was also done with samples that were incubated in the presence of SDS 2% or 2-ME 5% or iodacetamide 4 mM. The positive control was taken as the activity obtained with 0.23 μg papain, which was activated with 0.7 mM 2-ME in Tris-HCl 0.05M at pH 8.0 at 4° C. for 10 minutes and then at 37° C. for 15 minutes with frequent stirring. As negative control, reaction mixtures without extracts were used.

Using the insoluble substrate hide powder azure (Table 1), the activity of the crude extract was inhibited 67% with iodacetamide 4 mM. On the other hand, the IC:M fraction showed a reduced proteolytic activity of 92% to the crude extract activity. The IC:M fraction presented a slight recuperation in proteolytic activity in presence of 2% SDS and 5% 2-ME (0.322 units). As can be observed in Table 1, said recuperation was almost totally eliminated when the IC:M fraction was previously heated for 5 minutes (IC:MC fraction) and the proteolytic activity was not increased even in presence of SDS and 2-ME.

TABLE I

| TREATMENT | PROTEOLYTIC ACTIVITY UNITS (NORMALIZED) | ACTIVITY REDUCTION PERCENTAGE[a] |
| --- | --- | --- |
| Crude extract | 1.00[b] | 00 |
| Crude extract + iodacetamide | 0.33 ± 0.02 | 67 |
| IC:M fraction | 0.08 ± 0.06 | 92 |
| IC:M fraction + 2% SDS and | 0.32 ± 0.14 | 68 |

TABLE I-continued

| TREATMENT | PROTEOLYTIC ACTIVITY UNITS (NORMALIZED) | ACTIVITY REDUCTION PERCENTAGE[a] |
| --- | --- | --- |
| 5% 2-ME IC:M fraction heated (IC:MC) + 2% SDS and 5% 2-ME | 0.09 ± 0.11 | 91 |

[a]Reference based on the crude extract activity.
[b]1.00 = 0.750 ± 0.09 UOD (Units of Optical Density)

The study of amoebic molecules is difficult since they quickly degrade due the enzymatic activity of the proteases contained in *E. histolytica*; hence, it was verified that with this procedure there are many parasite molecules preserved. When analyzed electrophoretically, the crude extracts, the crude extracts with iodacetamide and the IC:MC fraction it was demonstrated that the IC:MC fraction preserves a great variety of molecules of low, medium and high molecular weight, which were stained with silver nitrate. The crude extract and the crude extract with iodacetamide contain low molecular weight peptides produced by the enzymatic degradation. The different extracts were electrophoretically analyzed in polyacrylamide gels with a linear gradient of 8–18% T 2.7C, in presence of SDS with the modified Maizel technique (Maizel, JR., J. V. (1971), "Polyacrylamide gel electrophoresis of viral proteins", in: Methods in Virology, Maramorosch, K. & Kaprowski, H (editors), New York: Academic Press, Vol. V, pp 798–246). Briefly: 5% packing gels were used. After a 20 minute pre-run at 50 V, 120 μg per cm of the amoebal extract were applied in a 0.049M Tris-HCl buffer pH of 6.8 containing 10% glycerol, 2% SDS, 0.015% bromophenol blue and 5% 2-ME. In each run known molecular weight markers were included. (Reagents of reactive grade (R) were used). After the run, part of the gel subjected to electrophoresis was separated to be stained with silver nitrate with modification to the Merril technique (Merril, C. R., Goldman, D., Sedman., S. A. & Eberb, M. (1981), "Ultrasensitive stain for proteins in polyacrylamide gel regional variations in cerebrospinal fluid proteins", Science, 211, 1434–1438). This portion of the gels were fixed with a 50% methanol: 12% acetic acid solution for 20 minutes; the gels were washed to eliminate the SDS excess with a 10% ethanol: 5% acetic acid solution, followed by three washings of 5 minutes each, with distilled water. Silver nitrate was added (0.02M) for 30 minutes. The bands were developed with sodium carbonate 0.28M, 0.05% formaline. The reaction was stopped with 1% acetic acid.

Figure 2:
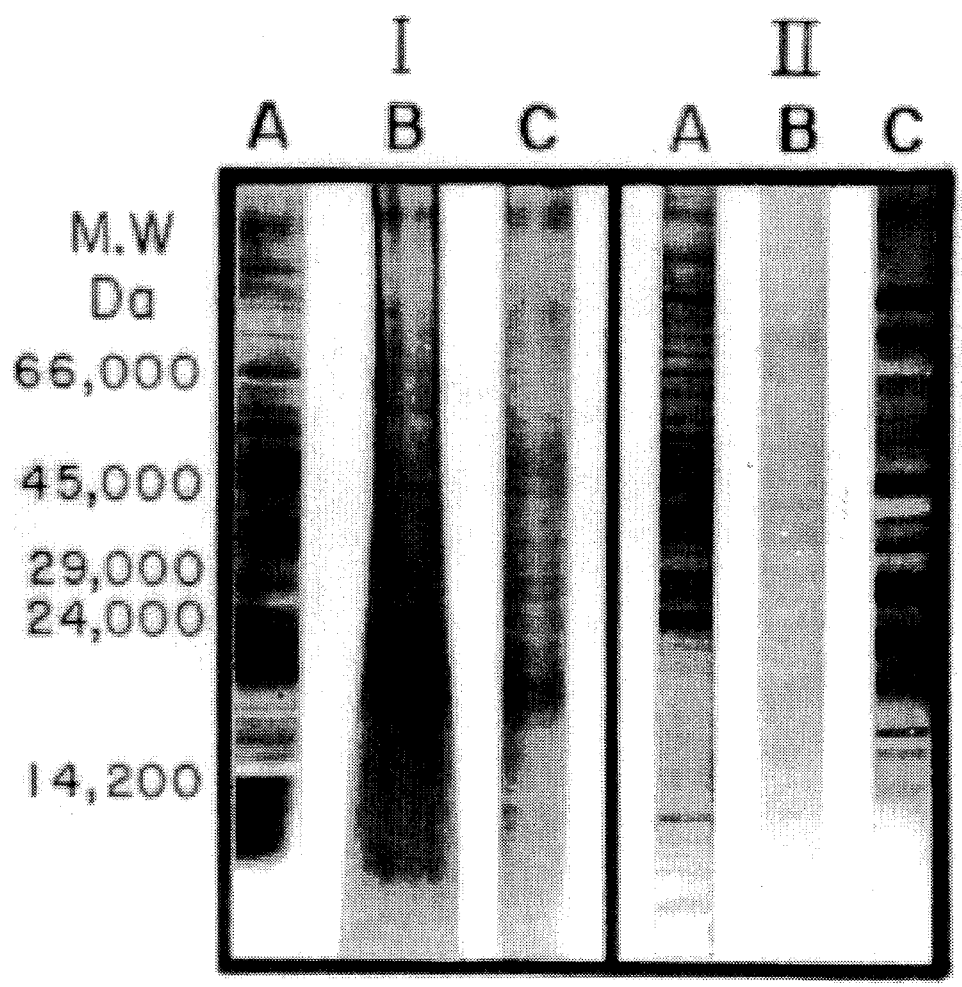
FIG. 2 shows I. Electrophoretic patterns in SDSPAGE. II. Electroimmunotransfer blot (EITB) patterns using serum from a patient with amebic liver abscess (ALA). A. IC:MC fraction. B. amebic crude extract. C. Amebic crude extract with iodoacetamide inhibitor.

In FIG. 2, lanes IB and IC show the electrophoretic patterns corresponding to the crude extract and to the crude extract + iodoacetamide and lane IA corresponds to the heated IC:M fraction (IC:MC). The IC:MC fraction presents the best resolution with a great variety of bands of different molecular weights. In the lane of the crude extract (IB) there are only a few bands observed; but at the front of the run a important stain that contains low molecular weight peptides which come from the enzymatic degradation of higher molecular weight molecules was observed. The crude extract lane with iodoacetamide (IC) presents more bands than the crude extract alone, but even so, it presents fewer bands than the IC:MC fraction. The crude extract with the enzymatic inhibitor iodoacetamide must be used quickly, whereas the IC:MC fraction can be conserved for several months.

The invented method is directed to the preservation of the antigens of without using a certain microorganism enzymatic inhibitors. One of the objectives of the present invention is the use of *Entamoeba histolytica* as a model to design a methodology able to preserve the antigens of the parasite and a further objective is to compare the obtained results with the invention method and show this is better than those obtained by conventional methods using enzymatic inhibitors. Therefore, this test verifies that the antibodies present in the sera of patients with amebic liver abscess (ALA) recognize and react with the molecules present in the extracts electrophoretically isolated. FIG. 2, II shows that the amebic molecules electrophoretically isolated according to their molecular weight, were electrotransferred to a nitrocellulose sheet according to Towbin et al. (Towbin, H., Staehelin, T. & Gordon J. (1979). "Electrophoretic transfer of proteins from polyacrylamide gels to nitrocellulose sheets: Procedure and some applications", Proceedings of the National Academy of Sciences, 76, 4350–4354), in an electrotransfer chamber (R) for 90 minutes at 1.0 amp final. After the transfer, the nitrocellulose membrane was blocked with 3% fish gelatine (R) in 0.15 M PBD pH 7.4. The sera to be analyzed were diluted to 1:50 in PBS with 0.3% gelatine and Tween 20 (R) 1:1000 and were incubated with the nitrocellulose sheet overnight at 4° C. This was developed with a polyvalent conjugate of total human anti-immunoglobulins bonded to peroxidase, in the presence of $H_2O_2$ substrate and 3,3 diaminobenzidine tetrahydrichloride as chromogen (R).

Also, it was demonstrated that the antigenic structure of the amboebal molecules is preserved in the IC:MC fraction obtained with the procedure described in this invention, since the antibodies of the sera of patients with amebic liver abscess (ALA) give antigen-antibody reaction bands with the electrotransfer preparations on nitrocellulose sheets (FIG. 2-II). More bands corresponding to antigenic reaction in the IC:MC fraction (FIG. 2-IIA) were observed than in the crude extracts (FIG. 2-IIB), in which only a few recognition bands were observed, since the major part of the antigens had been degraded by amebic enzymes, Also more bands in the heated IC:M fraction (IC:MC) were observed than in the crude extract with iodoacetamide (FIGS. 2-IIA, 2-IIC). This demonstrates that even in the presence of the inhibitor, many molecules are degraded whereas they are preserved in the IC:MC fraction with the method of the invention,

APPLICATION EXAMPLE

IDENTIFICATION THROUGH
IMMUNOELECTROTRANSFER (E.I.T.B.)
ANTIGENS OF *Entamoeba histolytica*,
RECOGNIZED ONLY BY SERA OF PATIENTS
WITH INVASIVE AMEBIASIS Sera were obtained by venous puncture from 32 adult persons of both sexes who attended at "Dr. Jose Eleuterio Gonzalez" University Hospital, in Monterrey Nuevo Leon, Mexico. Aliquots were taken and frozen at −20° C. until use.

For this study the sera were classified in the following groups:

Group 1. (32 cases). In this group were included the sera belonging to patients with amebic liver abscess (ALA) with a clinic picture consistent with ALA; with echography also consistent with ALA and with positive IHA test.

Group 2. (21 cases). In this group the sera of individuals with luminal intestinal amebiasis (IA) were included with positive coproparasitoscopic test and without clinical symptoms. To select this group, 3 coproparasitoscopic serial tests were made from 554 university students.

Group 3. (15 cases). Negative control. The sera were chosen from individuals who met the following criteria: lack of amebiasis symptoms, negative serial coproparasitoscopic test and negative IHA test and without any evidence of having suffered from symptomatic amebiasis.

COPROPARASITOSCOPIC TEST TO CHOOSE THE INDIVIDUALS FROM GROUP 2 AND 3

ANALYZED POPULATION: 554 students of the Universidad Autonoma de Nuevo Leon were studied, whose ages ranged from 16 to 19, belonging to the lower income classes.

FECAL SAMPLES: Three serial fecal samples of each individual were collected and conserved in 5% formol at 4° C. until their analysis under microscope.

METHOD USED: The Faust concentration and flotation method was used to obtain cysts, eggs and larvae of parasites. (Faust E. C., Russel P. E., Lincicome P. R. 1961. Parasitologia Clínica de Craig y Faust. 2. Edition, Mexico: UTEHA, 1056 ).

ANTIGENS OF *Entamoeba histolytica*

The trophozoites of *Entamoeba histolytica* strain HK-9, were cultured in a PHPS medium. (Said-Fernandez, S. Vargas-Villarreal, J., Castro-Garza, J., Mata-Cardenas, B., Navarro-Marmolejo L., Lozano-Garza, G., and Martinez-Rodriguez H., 1988, "PHPS medium: an alternative for axenic cultivation of *Entamoeba histolytica* and *E. invadens*", Trans. R, Soc. Trop. Med. Hyg. 83:29). The trophozoites were donated by Dr. Salvador Said-Fernandez Unidad de Investigaciones Biomédicas del Noreste IMSS Mexico.

AMOEBAL EXTRACTS: IC:MC FRACTION obtained according to the procedure of the present invention. The IC:M fraction obtained was vacuum dried and dissolved in tris HCl 0.049M buffer pH 6.8, containing 10% glycerol, 2% SDS, 0.015% bromophenol blue. The sample was subjected to a boiling water bath for 5 minutes, then aliquots were frozen at −70° C. Prior to use 5% 2-mercaptoethanol was added.

POLYACRYLAMIDE GELS (SDS-PAGE) and IMMUNOELECTROTRANSFERENCE (EITB): These experiments were made as described above.

DATA ANALYSIS: Each paper strip was examined individually and the migration distances were measured to calculate the Rf-value of each antigenic band. The molecular weights were calculated by interpolation on the obtained curves with commercially available markers of known molecular weight (Rf=distance of the protein migration/ distance of the dye migration).

INDIRECT HEMAGGLUTINATION TEST (IHA): This was made according to commercial kit instructions (Behring).

RESULTS

To select the sera of the individuals which would comprise groups 2 and 3 (intestinal amebiasis without symptoms and negative control) a serial coproparasitoscopic test of 554 students was made, and the results are shown in Tables 2 and 3. 74 individuals presented *Entamoeba histolytica*, representing 13.35% of the analyzed population. To comprise group sera of individuals only with *Entamoeba histolytica* were selected but those in which this protozoan was found with any pathogenic or commensal species were discarded for this study. (Flores-Castaneda M. S., Torres-Lopez E., Yanez-Rodriguez A., Medina De la Garza C., Salinas Carmona M. C. 1991, "Entero-parasitosis in a student population of the Monterrey N. L. Metropolitan area", Border Epidemiological Bulletin O.P.S. (W.H.O. No. 5:1–5).

TABLE 2

RESULTS OF THE COPROPARASITOSCOPIC TESTS MADE IN 554 INDIVIDUALS

| RESULTS | NUMBER |
| --- | --- |
| NEGATIVE | 382 (69%) |
| POSITIVE FOR PATHOGENIC SPECIES* | 109 (19.7%) |
| POSITIVE FOR COMMENSALS | 63 (11.3%) |

*including *Entamoeba histolytica*

TABLE 3

PROPORTION OF THE INDIVIDUALS WITH POSITIVE COPROPARASITOSCOPIC FOR *Entamoeba histolytica*

| SPECIES | NUMBER OF INDIVIDUALS |
| --- | --- |
| *Entamoeba histolytica* | 36 |
| *Entamoeba histolytica* + Any pathogenic species (a) | 5 |
| *Entamoeba histolytica* + Any commensal species (b) | 53 |

(a) association with *G. lamblia* or *Hymenolepsis nana*.
(b) association with *E. coli, E. nana. I. buetschlii*.

Figure 3:
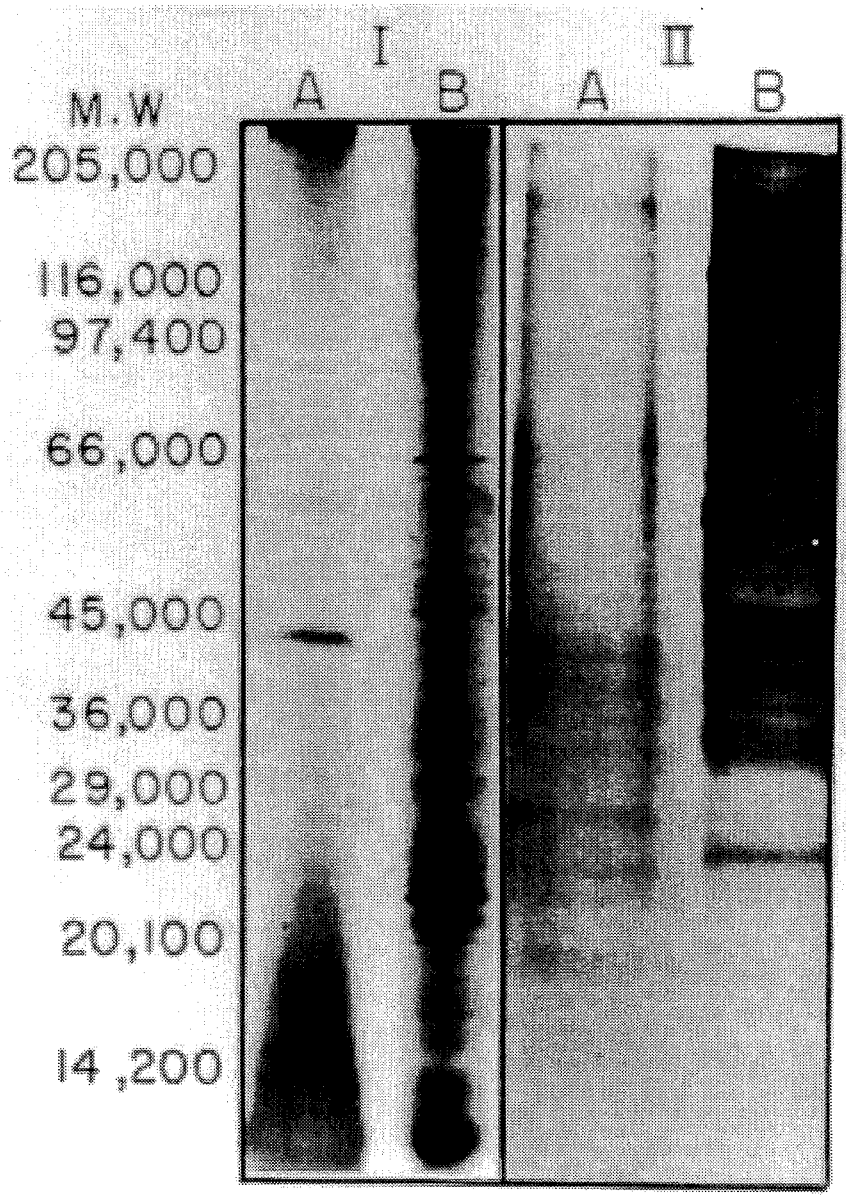
FIG. 3 shows the patterns of trophozoite extracts of *Entamoeba histolytica* HK-9. I. Electrophoretic patterns in gels of polyacrylamide-SDS stained with silver nitrate. II. EITB patterns, using the serum of a patient with amoebic liver abscess. A. Amebic crude extract. B. IC:MC fraction.

Electrophoesis in polyacrylamide gels were made of *Entamoeba histolytica* crude extracts and the IC:MC fraction. The results are shown in FIG. 3. A better resolution was obtained with the IC:M fraction, in the gels stained with silver nitrate (IB) as in the EITB (IB, IIB). In FIG. 3 (IB) it can be observed that the obtained electrophoretic pattern is very complex and presents bands of molecules with molecular weights between 8 Kd and 200 Kd. We also verified that not all the amoebic molecules are recognized by the serum of the patient with ALA used in this EITB (IIB compared with IB), which seems to indicate that not all the amoebic molecules are immunogenic. The *Entamoeba histolytica* proteases are very active; the spot which appeared at the front of the crude extract are random enzymatic degradation products, which are not observed in the IC:MC fraction.

Figure 4:
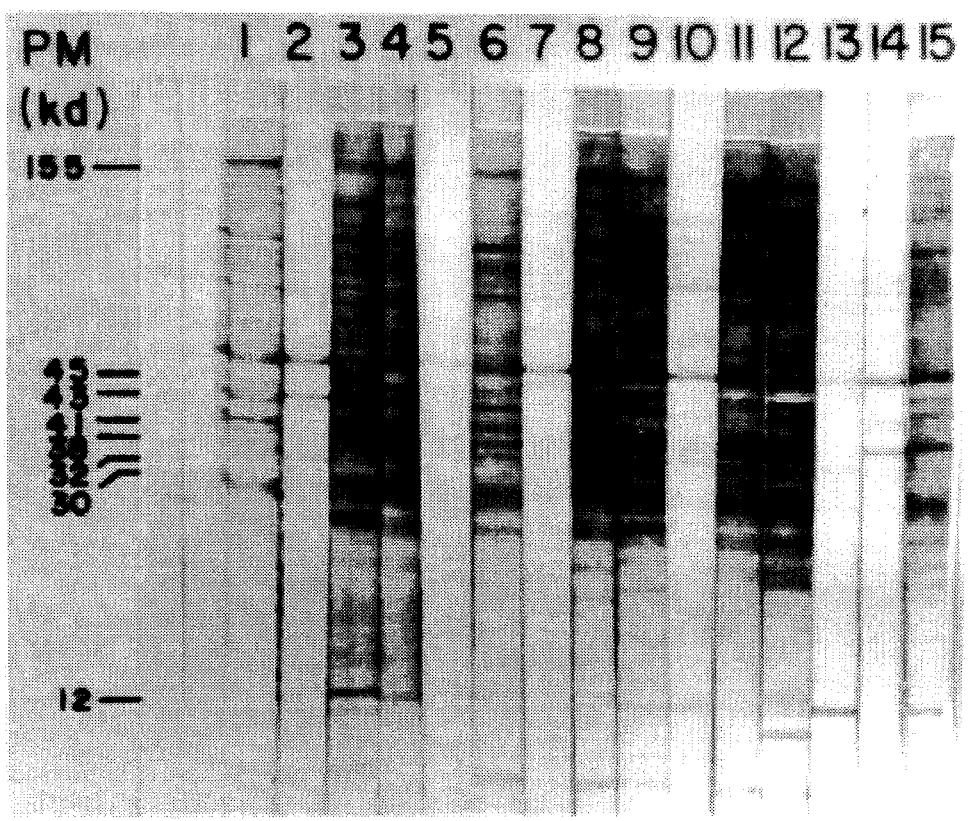
FIG. 4 shows the EITB patterns obtained with the anti-amoeba antibodies present in the sera of individuals with amebiasis. Amebic liver abscess (ALA). 3, 4, 6, 8, 9, 11, 12 and 15 Intestinal amebiasis (I.A.); 1, 2, 10, 13 and 14; Negative control sera 5 and 7.

To determine the molecular weight relative to the immunodominant bands, the IC:MC fraction was analyzed by SDS-PAGE and EITB and the antigen-antibody reaction bands obtained with sera from Groups 1, 2, and 3 were correlated to the protein bands on the SDS-PAGE gels. From this data, antigenic reference patterns were identified for each group of sera. Always a more intense reactivity with the ALA sera compared with that obtained with the IA sera (FIG. 4) was obtained. The A.I. sera and the negative control sera give reaction bands but weaker ones. This finding was expected since Mexico is an amebiasis endemic. The results allowed the identification of bands that are recognized by all the sera and have relative molecular weight of 45, 43, 42, 39, 38, 32, 31 and 12 Kd. Some bands are recognized only by the ALA and IA sera and have relative molecular weights of 150, 29, 21, 20, 17, 16, 14 and 13 Kd. One of the most relevant aspects of the present invention is the identification of an antigenic pattern recognized exclusively and selectively by sera from amebic liver abscess (ALA) patients. The EITB pattern exclusive for ALA includes bands with molecular weights of 23, 25, 37, 11, 10, 9 and 8 Kd, which are only recognized by the sera of patients with amebic liver abscess. No sera of patients with IA recognized these bands (FIG. 4: lanes 1, 10, 13).

The three groups of proteins that are identified by the patient Groups 1, 2 and 3 can be considered to be antigenic reference patterns identified exclusively and selectively in sera from ALA patients, identified in sera from both ALA and IA patients or identified in all sera tested including negative control sera.

If it is assumed that only invasive amebiasis (ALA) induces protection against further amebic reinfections, it can be assumed that the antigens of the ALA EITB patterns may play an important role in immune protection against amoebas. The identified characteristic ALA-EITB pattern is useful to differentiate the invasive amebiasis (ALA) patients sera, from those with non invasive intestinal amebiasis (IA). The EITB patterns could provide knowledge of amoebic antigens involved in induction of immune response against *Entamoeba histolytica*.

I claim:

1. A method of determining an antigenic reference pattern of proteins selectively recognized by sera from patients having amebic liver abscesses comprising:

culturing trophozoites of *E. histolytica* axenically;

extracting an insoluble fraction from the trophozoites with polar solvents;

drying the insoluble fraction to eliminate residues of the solvents;

suspending the dried fraction in a buffer;

heating the buffered suspension for a sufficient time and at a sufficient temperature to yield preserved antigens of *E. histolytica* which do not require the presence of enzymatic inhibitors;

separating the preserved antigens on SDS-PAGE to obtain an antigenic pattern of the preserved antigens;

electrotransferring the antigenic pattern of the preserved antigens to at least three membranes;

incubating one of the membranes with a sample of human serum from a patient diagnosed as having amebic liver abscesses, incubating another one of the membranes with a sample of human serum from a patient diagnosed as having intestinal amebiasis and incubating another one of the membranes with a sample of human serum from a patient diagnosed as being negative for any clinical symptoms of or for diagnostic tests of any amebic disease, wherein said incubations are performed for a sufficient period of time and under sufficient conditions to allow antibody-antigen binding;

detecting the antibody-antigen binding;

correlating the detected antibody-antigen binding on the electrotransferred membranes to the corresponding protein bands in the antigenic pattern of the preserved antigens;

identifying the antigens which result in positive antibody-antigen binding with each of the samples of human serum; and determining the antigens which are positive only with the sample of human serum from the patient diagnosed as having amebic liver abscesses and which are negative with the sample of human serum from the patient diagnosed as having intestinal amebiasis and with the sample of human serum from the patient diagnosed as being negative for any clinical symptoms of or for diagnostic tests of any amebic disease in order to provide an antigenic reference pattern of the proteins selectively recognized by sera from patients with amebic liver abscesses.

2. The method of claim 1, wherein the antigens positive only with the sample of human serum from the patient diagnosed as having amebic liver abscesses have a molecular weight in kDs of 8, 9, 10, 11, 23, 25, or 37.

3. The method of claim 1, wherein the polar solvent is chloroform, methanol, ether, ethanol or mixtures thereof.

4. The method of claim 3, wherein the polar solvent is a mixture of chloroform and methanol.

5. The method of claim 1, wherein the heating of the buffered suspension is performed in a boiling water bath for from approximately 2 to 20 minutes.

6. A method of aiding in the differential diagnosis of a patient with amebic liver abscesses by detecting the presence of antibodies in a sample of human serum which bind to *Entamoeba histolytica* antigens identified in an antigenic reference pattern as selectively recognized by sera from patients with amebic liver abscesses comprising:

culturing trophozoites of *E. histolytica* axenically;

extracting an insoluble fraction from the trophozoites with polar solvents;

drying the insoluble fraction to eliminate residues of the solvents;

suspending the dried fraction in a buffer;

heating the buffered suspension for a sufficient time and at a sufficient temperature to yield preserved antigens of *E. histolytica* which do not require the presence of enzymatic inhibitors;

separating the preserved antigens on SDS-PAGE to obtain an antigenic pattern of the preserved antigens;

electrotransferring the antigenic pattern of the preserved antigens to a membrane;

incubating the membrane with the sample of human serum for a sufficient period of time and under conditions sufficient to allow antibody-antigen binding;

detecting the antibody-antigen binding;

correlating the detected antibody-antigen binding on the electrotransferred membrane to the corresponding protein bands in the antigenic pattern of the preserved antigens; and identifying the samples of human serum containing antibodies which bind to at least one *E. histolytica* antigen identified in an antigenic reference pattern as selectively recognized by sera from patients with amebic liver abscesses.

7. The method of claim 6, wherein the *E. histolytica* antigens identified in an antigenic reference pattern as selectively recognized by sera from patients with amebic liver abscesses have a molecular weight in kDs of 8, 9, 10, 11, 23, 25, or 37.

8. The method of claim 6, wherein the polar solvent is chloroform, methanol, ether, ethanol or mixtures thereof.

9. The method of claim 8, wherein the polar solvent is a mixture of chloroform and methanol.

10. The method of claim 9, wherein the heating of the buffered suspension is performed in a boiling water bath for from approximately 2 to 20 minutes.

11. A method of aiding in the differential diagnosis of a patient with intestinal amebiasis by detecting the presence of antibodies in a sample of human serum which bind to *Entamoeba histolytica* antigens identified in an antigenic reference pattern as indicative of both amebic liver abscesses and intestinal amebiasis and but not identified in an antigenic reference pattern as selectively recognized only by sera from patients with amebic liver abscesses comprising:

culturing trophozoites of *E. histolytica* axenically;

extracting an insoluble fraction from the trophozoites with polar solvents;

drying the insoluble fraction to eliminate residues of the solvents;

suspending the dried fraction in a buffer;

heating the buffered suspension for a sufficient time and at a sufficient temperature to yield preserved antigens of *E. histolytica* which do not require the presence of enzymatic inhibitors;

separating the preserved antigens on SDS-PAGE to obtain an antigenic pattern of the preserved antigens;

electrotransferring the antigenic pattern of the preserved antigens to a membrane;

incubating the membrane with the sample of human serum for a sufficient period of time and under conditions sufficient to allow antibody-antigen binding;

detecting the antibody-antigen binding;

correlating the detected antibody-antigen binding on the electrotransferred membrane to the corresponding protein bands in the antigenic pattern of the preserved antigens;

identifying the samples of human serum containing antibodies which bind to at least one *E. histolytica* antigen identified in an antigenic reference pattern as indicative of both amebic liver abscesses and intestinal amebiasis;

further identifying the samples of human serum identified in the previous first identification step, containing antibodies which bind to at least one *E. histolytica* antigen identified in an antigenic reference pattern as selectively recognized only by sera from patients with amebic liver abscesses indicative of amebic liver abscesses; and selecting the samples of human serum as being indicative of a patient with intestinal amebiasis as said samples not being identified in the previous second identification step by binding to at least one *E. histolytica* antigen identified in an antigenic reference pattern as selectively recognized only by sera from patients with amebic liver abscesses.

12. The method of claim 11, wherein the *E. histolytica* antigens identified in an antigenic reference pattern as indicative of both amebic liver abscesses and intestinal amebiasis have a molecular weight in kDs of 150, 29, 21, 20, 17, 16, 14 or 13.

13. The method of claim 11, wherein the *E. histolytica* antigens identified in an antigenic reference pattern as selectively recognized only by sera from patients with amebic liver abscesses have a molecular weight in kDs of 8, 9, 10, 11, 23, 25, or 37.

14. The method of claim 11, wherein the polar solvent is chloroform, methanol, ether, ethanol or mixtures thereof.

15. The method of claim 14, wherein the polar solvent is a mixture of chloroform and methanol.

16. The method of claim 11, wherein the heating of the buffered suspension is performed in a boiling water bath for from approximately 2 to 20 minutes.

* * * * *